(12) United States Patent
Kelly et al.

(10) Patent No.: US 7,452,965 B2
(45) Date of Patent: Nov. 18, 2008

(54) COLON TUMOR SPECIFIC BINDING PEPTIDES

(75) Inventors: Kimberly A. Kelly, Burlington, MA (US); David A. Jones, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 17 days.

(21) Appl. No.: 10/510,155

(22) PCT Filed: Apr. 7, 2003

(86) PCT No.: PCT/US03/10630

§ 371 (c)(1),
(2), (4) Date: Jul. 11, 2005

(87) PCT Pub. No.: WO03/086284

PCT Pub. Date: Oct. 23, 2003

(65) Prior Publication Data

US 2006/0058228 A1    Mar. 16, 2006

Related U.S. Application Data

(60) Provisional application No. 60/369,850, filed on Apr. 5, 2002.

(51) Int. Cl.
*A61K 38/12* (2006.01)
(52) U.S. Cl. .......................... 530/317; 514/12
(58) Field of Classification Search ............... None
See application file for complete search history.

(56) References Cited

U.S. PATENT DOCUMENTS

| 5,190,920 A | 3/1993 | Eyal et al. | 514/17 |
| 5,985,240 A | 11/1999 | Zamora et al. | 424/1.65 |
| 6,277,818 B1 * | 8/2001 | Mazar et al. | 514/9 |

FOREIGN PATENT DOCUMENTS

| EP | 0896003 | 2/1999 |
| EP | 0906919 | 4/1999 |
| WO | WO 01/77145 | 10/2001 |

OTHER PUBLICATIONS

Wolfe HR, Mendizabal M, Lleong E, Cuthbertson A, Desai V, Pullan S, Fujii DK, Morrison M, Pither R, Waldman SA. In vivo imaging of human colon cancer xenografts in immunodeficient mice using a guanylyl cyclase C—specific ligand. J Nucl Med. Mar. 2002;43(3):392-9.*
Charles K. Brown, MD et al., "A Novel Approach for the Identification of Unique Tumor Vasculature Binding Peptides Using an *E. coli* Peptide Display Library", Annals of Surgical Oncology, 2000, pp. 743-749, vol. 7, No. 10.
Jin Gui et al., "Selection of a Peptide with Affinity for the Tumor-Associated TAG72 Antigen from a Phage-Displayed Library", Biochemical and Biophysical Research Communications, 1996, pp. 414-419, vol. 218, Article No. 0072.
Kimberly A. Kelly et al., "Isolation of a Colon Tumor Specific Binding Peptide Using Phage Display Selection", Neoplasia, Sep./Oct. 2003, pp. 437-444, vol. 5, No. 5.
Fukuto Maruta et al., "Identification of FGF receptor-binding peptides for cancer gene therapy", Cancer Gene Therapy, 2002, pp. 543-552, vol. 9.
Ulla B. Rasmussen et al., "Tumor cell-targeting by phage-displayed peptides", Cancer Gene Therapy, 2002, pp. 606-612, vol. 9.
Erkki Ruoslahti "Targeting tumor vasculature with homing peptides from phage display", Cancer Biology, 2000, pp. 435-442, vol. 10.
Koivunen et al., Isolation of a Highly Specific Ligand for the $\alpha_5\beta_1$ Integrin from a Phage Display Library, Journal of Cell Biology 124(3):373-380 (1994).

* cited by examiner

*Primary Examiner*—Larry R. Helms
*Assistant Examiner*—Meera Natarajan
(74) *Attorney, Agent, or Firm*—Ballard Spahr Andrews & Ingersoll, LLP

(57) ABSTRACT

Phage display was used to screen peptide libraries that distinguish between well-differentiated (HCT116) and poorly-differentiated colon carcinoma cells (HT29). The screening protocol used selection and subtraction on intact, viable cells, resulting in phage libraries exhibiting high binding selectivity for the poorly-differentiated HT29 cells. A nine amino acid, disulfide-constrained peptide (RPM) was identified that selectively bound and was internalized into colon cancer cells. The peptide may be used to detect colon cancer cells and also may be used to selectively deliver therapeutic agents to the cells.

14 Claims, 12 Drawing Sheets

The HT29 mature phage pool is selective for HT29 cellsthe amplified phage pool generated from each round of maturation. Phage remaining bound were quantified by real time PCR.

HT29 or HCT116 cells were incubated with $10^{10}$ pfu from

FIG. 3

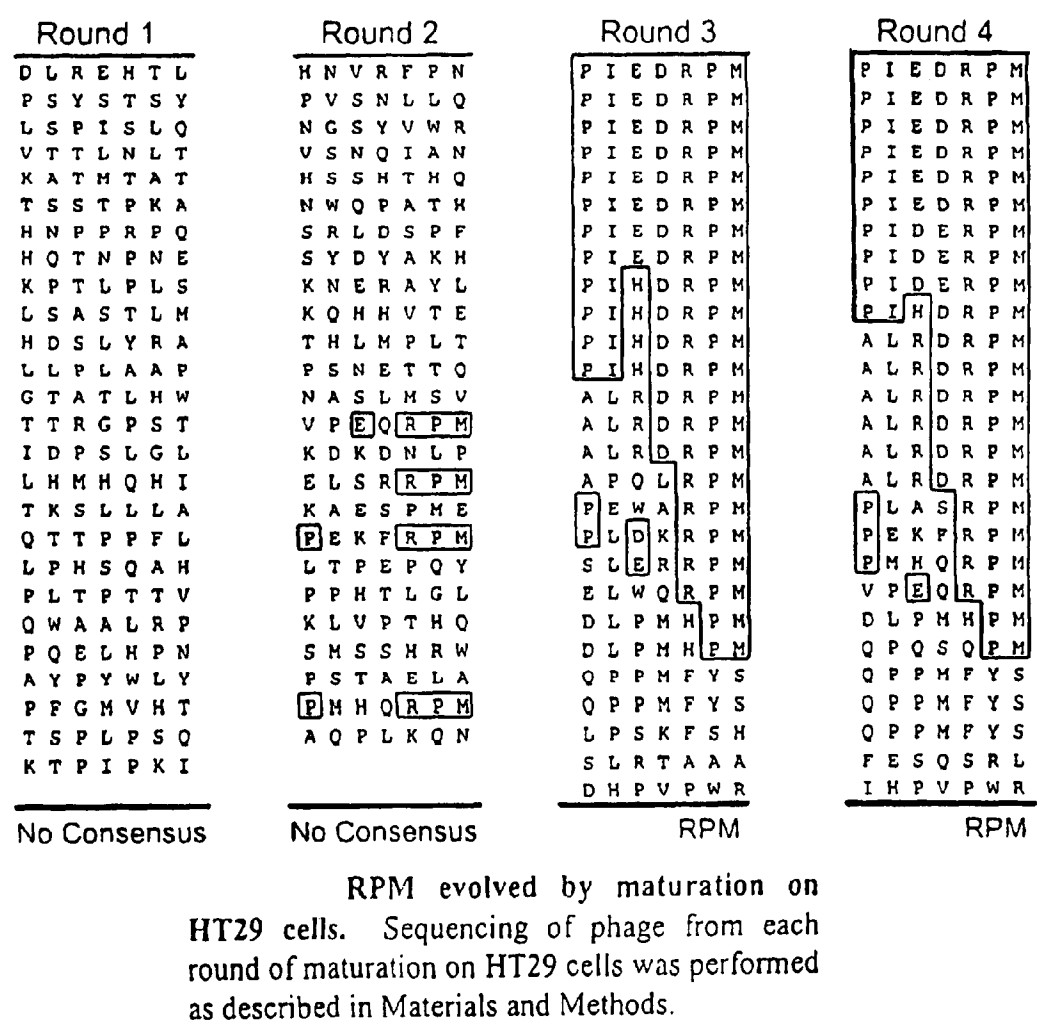

RPM evolved by maturation on HT29 cells. Sequencing of phage from each round of maturation on HT29 cells was performed as described in Materials and Methods.

FIG. 4

- CPIEDRPMC Phage
- CPIDERPMC Phage
- CALRDRPMC Phage
- CPEKFRPMC Phage
- CSPQSQPMC Phage

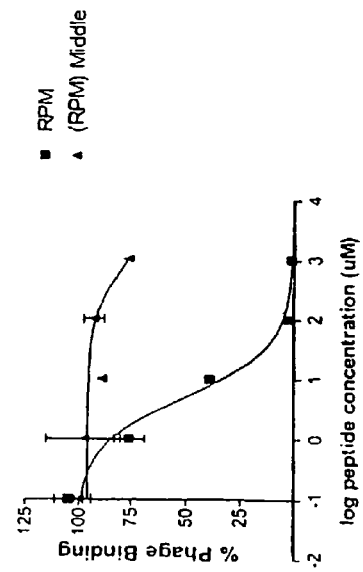

Binding to HT29 cells is dependent on the three amino acids, RPM, and their position within the peptide. A. HT29 cells were incubated with the $10^{10}$ PFU of indicated phage and increasing log concentrations of CPIEDRPMC peptide. B. As above, HT29 cells were incubated with RPM phage and increasing log concentrations of peptides with alanine mutations in the RPM sequence. C. HT29 cells were incubated with the indicated concentration of either CPIEDRPMC (RPM) or CPIRPMEDC (RPM middle) peptide and $10^{10}$ pfu of RPM phage. In all panels, the number of phage remaining bound to the cells was quantified by real time PCR.

A.

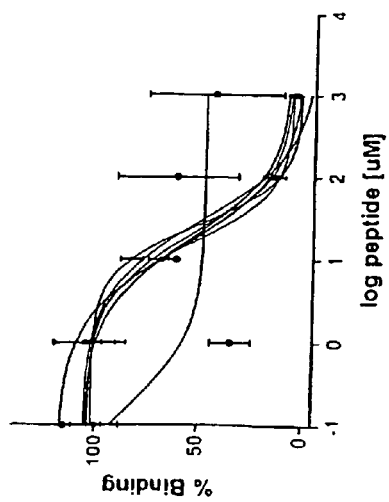

B.

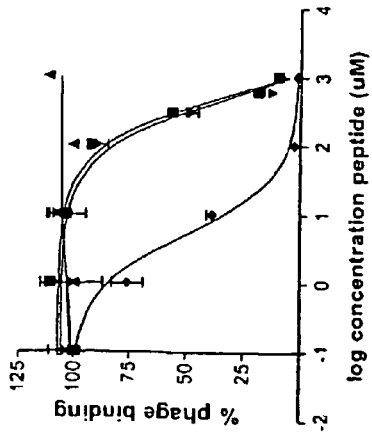

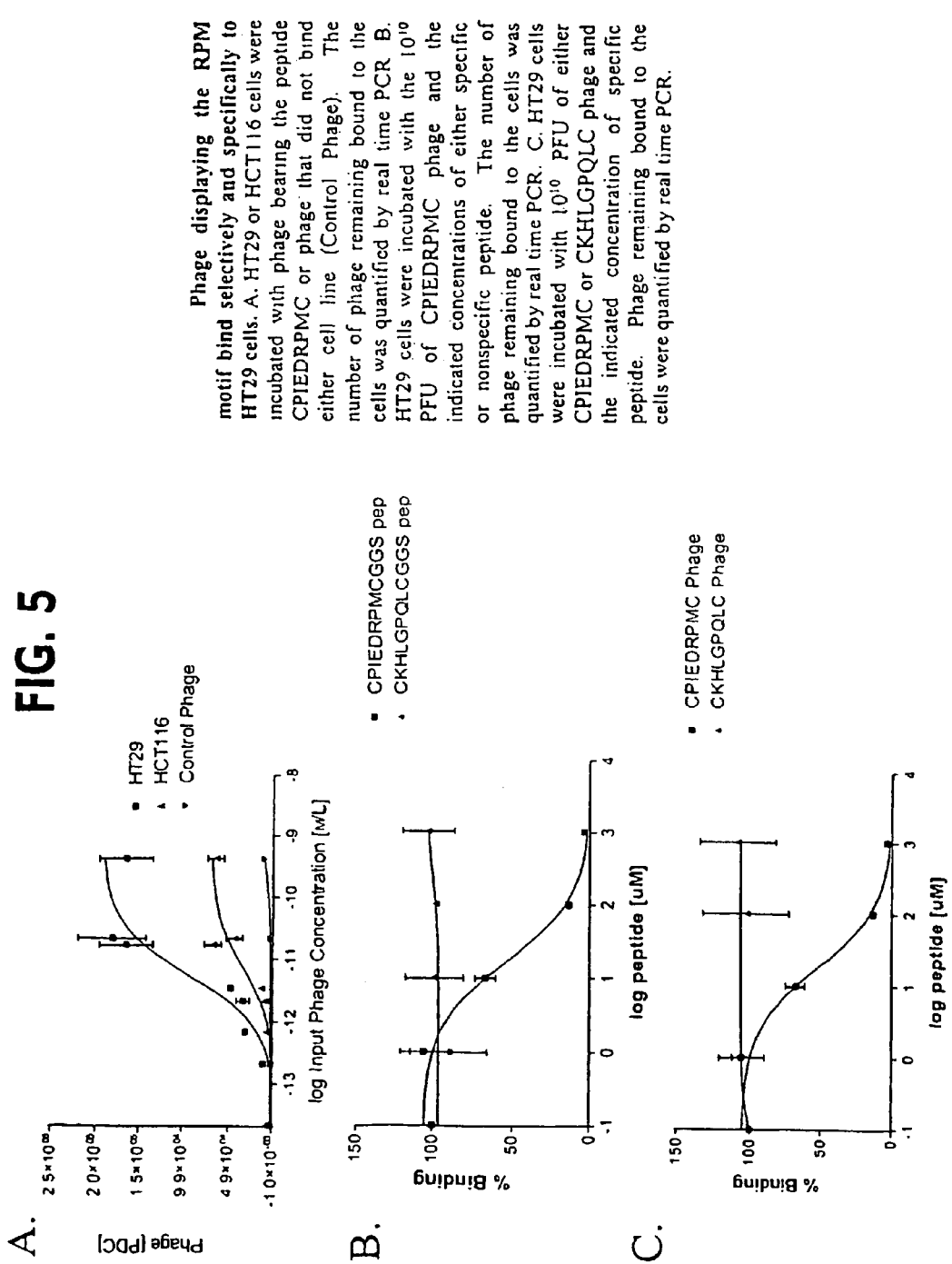

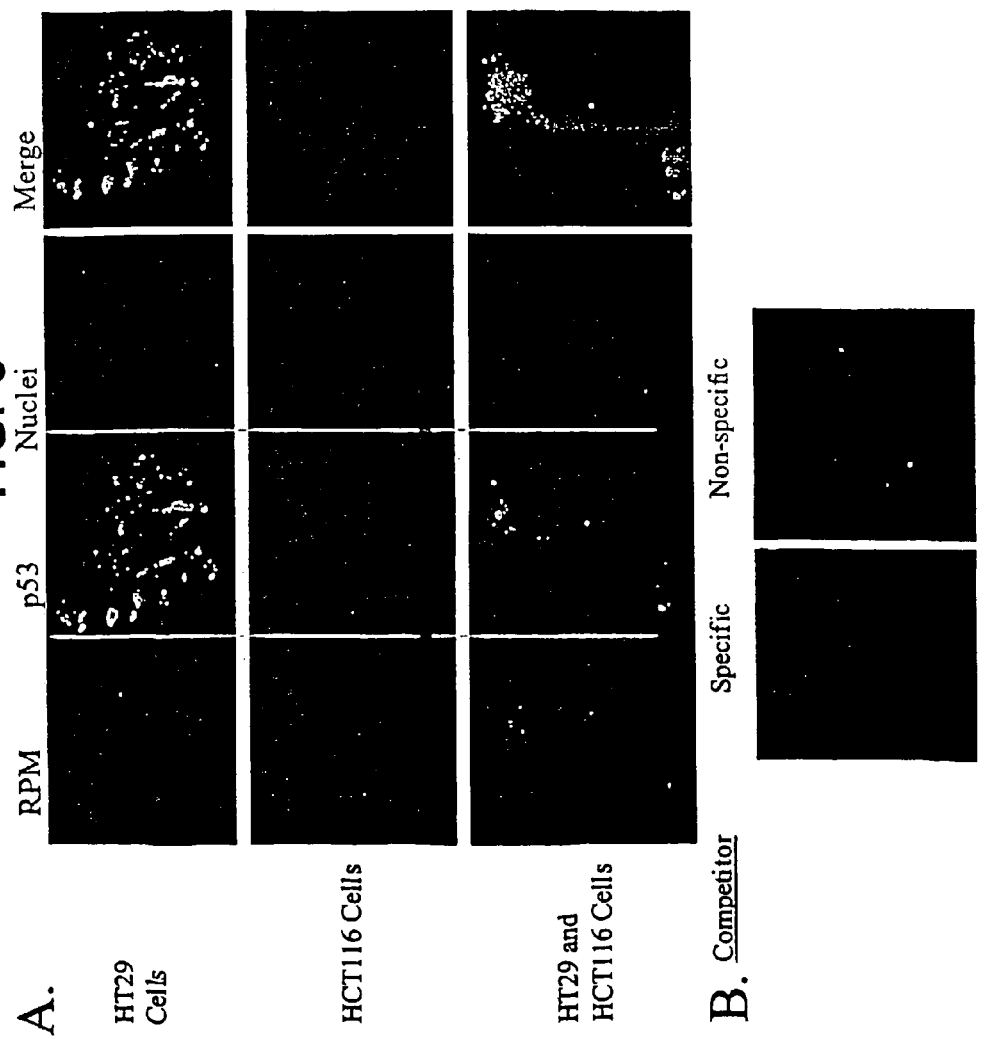

FIG. 6 RPM peptide binds selectively to HT29 cells. A. A well of HT29, HCT116, or a mixture of 50% HT29 and HCT116 cells were incubated with FITC-RPM (red), fixed then incubated with a monoclonal antibody to p53 (green). Slides were analyzed by confocal microscopy. Nuclei are colored blue. B. Competition assay. HT29 cells were incubated with FITC-RPM in the presence of excess unlabeled specific or unlabeled non-specific competitor then analyzed by confocal microscopy.

FIG. 7

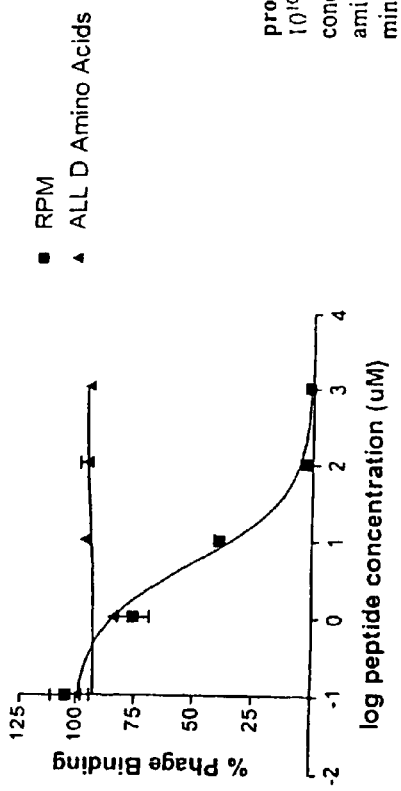
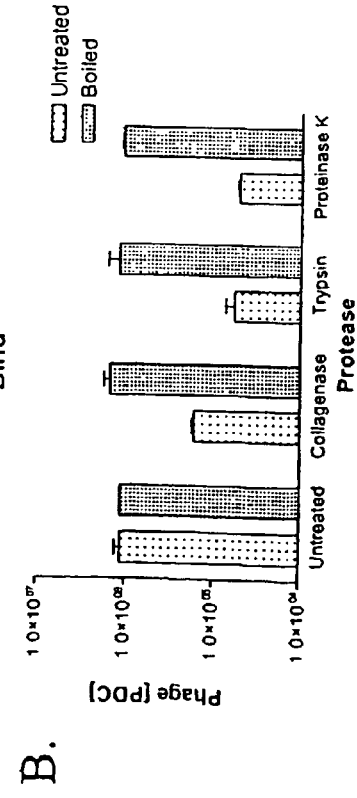

RPM peptide binds to a HT29 protein. A. HT29 cells were incubated with the 10^10 PFU of RPM phage and increasing log concentrations of RPM peptide containing all D amino acids. B. HT29 cells were incubated for 15 minutes with collagenase, 5 minutes with Trypsin, or 1 minute with Proteinase K. As a control, the proteases were boiled for 15 minutes and then cells were incubated with the boiled proteases as above. After incubation with the respective protease, cells were incubated with 10^10 pfu of RPM phage. C. The effect of protease incubation on HT29 viability was determined using an MTT assay. Cells were treated with proteases as in A. After treatment, MTT was added to a final concentration of 250 ug/mL and incubated for 45 minutes at 37 C. Following incubation with MTT, incorporation of the dye by the cells was assayed by plate reader set to absorb at 570nm. In A and B, the number of phage remaining bound were quantified by real time PCR.

RPM localizes to the cell surface at 4°C and is internalized at 37 °C. A. HT29 cells were incubated with FITC-RPM at 4°C then analyzed by confocal microscopy. B. Representative field of the FITC-RPM (green) and the β Catenin (red) immunostained HT29 cells. (4°C) C. HT29 cells were incubated with FITC-RPM at 37 °C then analyzed by confocal microscopy.

FIG. 9
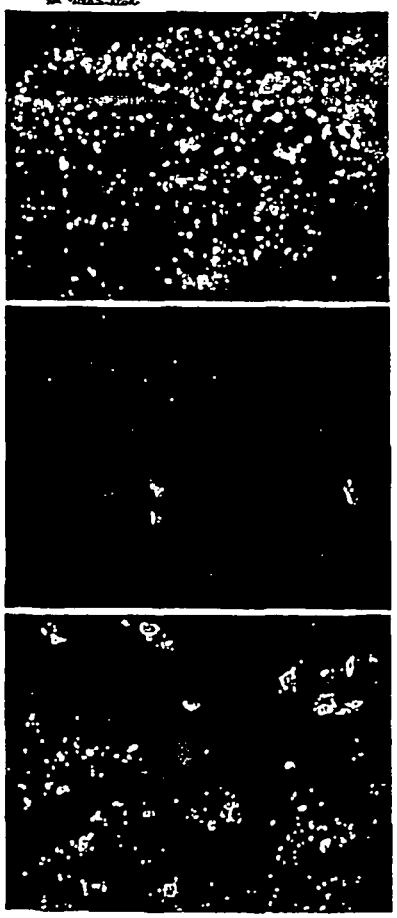
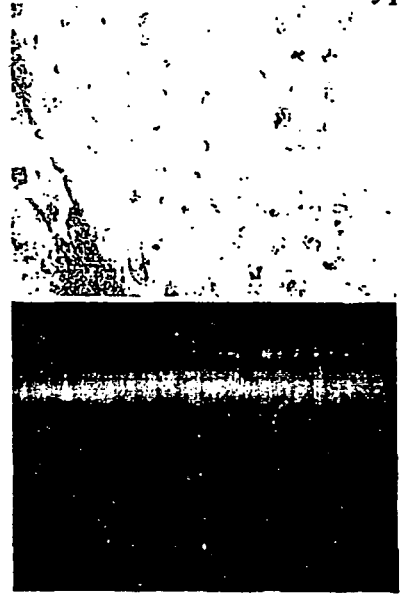
RPM binds to colon tumors. Sections of matched human colon tumor or normal were incubated with the indicated reagent then analyzed by: H&E- light microscopy (10x) and Fluorescence- confocal microscopy (60x).

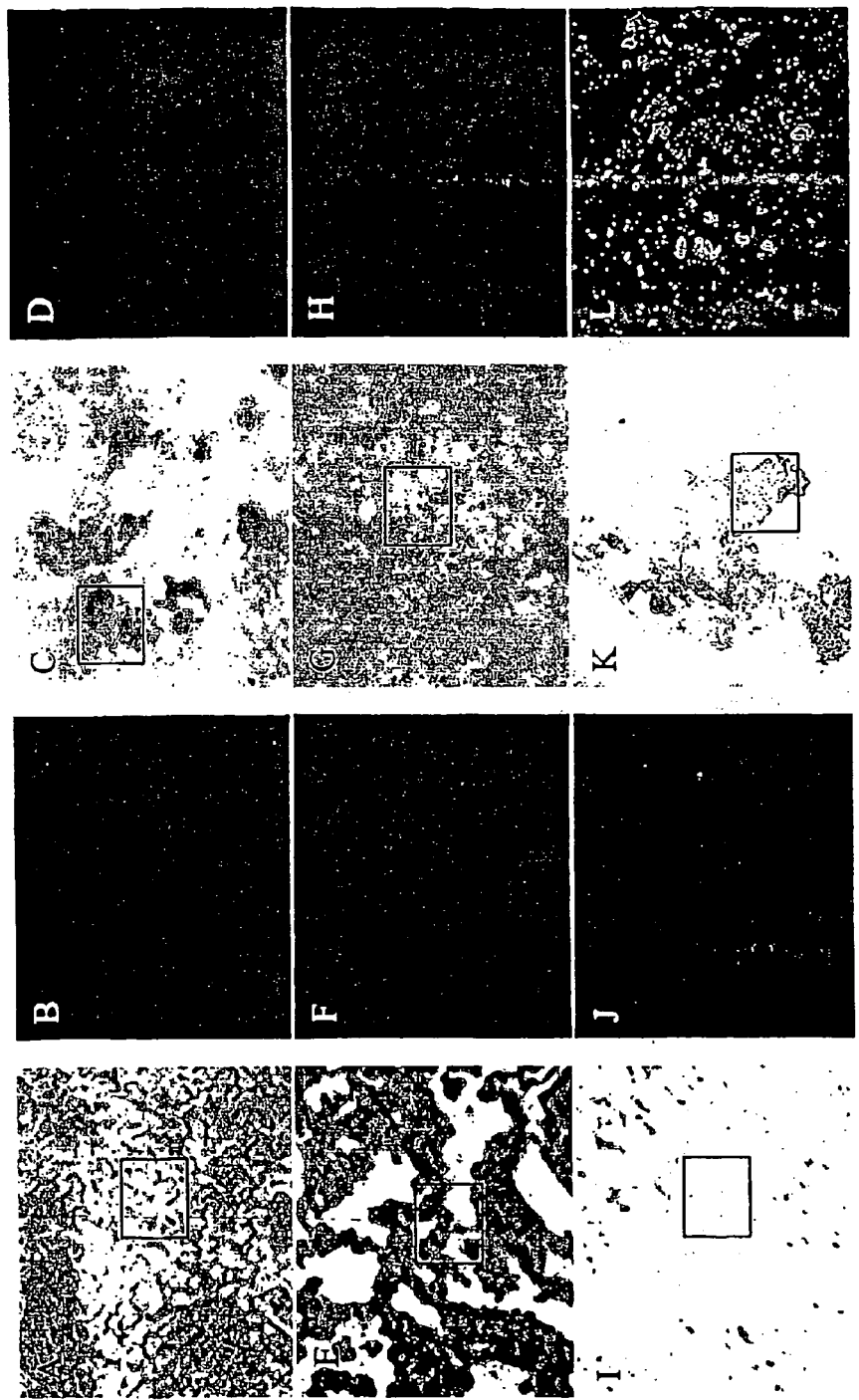

FIG. 10

RPM does not bind to normal lung, liver or stomach or to liver or lung cancer. A and B. Grossly univolved liver. C and D. Liver sarcoma. E and F. Grossly univolved lung. G and H. Lung sarcoma. I and J. Normal Stomach. K and L Colon Tumor. B,D,F,H,J, and L. Fluorescence microscopy of indicated tissues incubated with RPM-FITC and Topro-3. (60x). A,C,E,G,I, and K. H&E staining of the corresponding views (10x).

FIG. 11

RPM-KLAK and KLAK on HT29 and HCT116 cells (MTT assay)

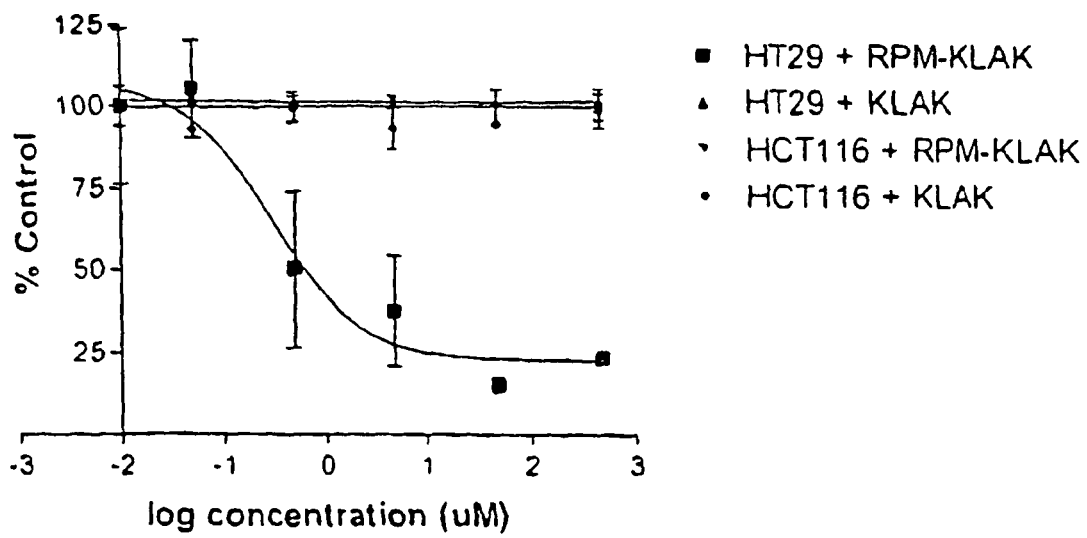

- HT29 + RPM-KLAK
- HT29 + KLAK
- HCT116 + RPM-KLAK
- HCT116 + KLAK

RPM-KLAK kills HT29 cells. HT29 and HCT116 cells were incubated with increasing log concentrations of either RPM-KLAK or KLAK for 72 hours at 37°C. After incubation, cell viability was determined by MTT assay. The percentage viability was determined by dividing the absorbance units of a sample well by the absorbance units of the vehicle treated well.

FIG. 11 (Cont.)

Material and Method for selection and subtraction: An aliquot of the complete phage library from NEB was incubated with 2x105 cells (step 1). B. Phage that bound were eluted and incubated with the same number of HCT116 cells for a total of 5 incubations (steps 2-6). The phage that bound the HCT116 cells was eluted and the number of plaque forming units was determined by real time PCR. C. The number of phage that did not bind the HCT116 cells after five rounds of depletion was determined . The phage were amplified (step 8) then incubated with 2x 105 HT29 cells. Cells were washed to remove unbound phage and the bound phage was eluted. The number of phage bound was determined and the remaining eluate was amplifed. The amplified phage was used with the same number of HT29 cells and the process was repeated (steps 9-12) for a total of five rounds of maturation.

COLON TUMOR SPECIFIC BINDING PEPTIDES

This application claims priority to U.S. Provisional Application Ser. No. 60/369,850 filed Apr. 5, 2002 which is hereby incorporated by reference in its entirety.

BACKGROUND OF THE INVENTION

Colon carcinogenesis is thought to be a stepwise process that involves the transition of normal colon epithelium to neoplasm. The multistep progression of the disease requires years and possibly decades, and therefore apparently provides ample time for diagnosis and treatment. Unfortunately, however, 63% of colon cancer remains undetected until it has spread to the surrounding organs or lymph, a finding that correlates with a poor prognosis. In the gastrointestinal tract, conventional endoscopic techniques do not provide sufficient contrast for sensitive and reliable identification of early tumor disease.

One of the earliest recognizable events in the transition of normal colon epithelial cells into a carcinoma is the alteration of the cell kinetic processes of proliferation, differentiation, and apoptosis within the epithelial cells comprising the colon crypt. The zone of proliferation expands and ultimately encompasses the entire crypt. Moreover, the level of apoptosis is reduced and cannot balance the increased proliferation that occurs. The expansion of the proliferation zone is thought to result in the formation of a polyp that is composed of poorly-differentiated colonocytes and represents an intermediate stage in the development of a carcinoma. The transformation to carcinoma often is characterized by acquisition of an invasive phenotype wherein defective cells invade the underlying basement membrane.

Recent research has shed light on the genetic events that accompany the progression of normal colonic epithelium to neoplasm. In approximately 85% of sporadic colon cancers and in all inherited cases of familial adenomatous polyposis (FAP) forms of colon cancer have mutated adenomatous polyposis coli, APC. Further, in both sporadic tumors and FAP, mutations in APC were identified at the earliest stages of neoplasia, aberrant crypt foci These findings suggest that defects in the APC gene are the initiating event in the onset of the majority of colon tumors. In fact, APC appears to control colonic cell kinetics and seems to be involved in the first steps of colon carcinogenesis, particularly in the transition from normal to hyperproliferative colonocytes.

In light of the role played by the APC gene during colon tumorigenesis, it would be helpful to understand the functions of the APC protein. The APC protein is a large multidomain protein with many protein-protein interaction domains. It has been shown that APC binds to β-catenin, a protein that functions in cell adhesion and Wnt-based signal transduction. More than 90% of APC gene mutations inactivate the gene, resulting in premature termination of the transcript and subsequent truncation of the APC protein. Truncated APC proteins often retain the ability to dimerize and bind β-catenin, but lose the capacity to phosphorylate and alter intracellular levels of β-catenin and to bind to the microtubule cytoskeleton.

The failure of β-catenin levels to be properly regulated by proteasome degradation, and the subsequent increase of β-catenin-TCF complex formation results in an alteration of gene transcription. Functional β-catenin-TCF binding sites have been identified in the promoters of the cell cycle regulatory genes, cyclin D1 and c-myc and the overexpression of APC protein has been shown to block the cell cycle progression from the g0 and g1 phases to the s phase. Therefore, APC protein appears to have an important role in the regulation of colonic cell proliferation. Thus, the inactivation of the APC gene appears to disrupt both cell-cell and cell-matrix interaction, leading to inappropriate proliferation.

Through genetics, clinicians are able to identify patients that have an inherent risk for developing colon cancer. Although clinicians and researchers have identified an underlying molecular cause of colon cancer, this knowledge has translated into modest clinical success in the early diagnosis and treatment of colon cancer. Early work has focused on the use of antibodies for tumor recognition and drug delivery. However, when antibodies are used as the targeting molecule, the immunogenicity and long plasma half-life of these proteins were detrimental.

Currently, colon cancer detection methods are limited to recognition of relatively large abnormalities by visual inspection. Improved detection sensitivity through the use of diagnostic tools—such as high affinity peptides that exploit the molecular differences between normal, well-differentiated colonocytes and poorly-differentiated tumor cells—would be desirable.

It is apparent, therefore, that new methods that allow the accurate and convenient detection of neoplasms would dramatically extend life expectancy of many patients through disease prevention and are greatly to be desired. In particular, improved early detection methods that exploit the molecular differences between normal, well-differentiated colonocytes and neoplastic, poorly-differentiated colonocytes are highly desirable. Moreover, new methods of treating colon tumors are greatly to be desired.

SUMMARY OF THE INVENTION

Accordingly, it is an object of the invention to provide molecules that are selective or specific for colon tumors.

It is another object of the invention to provide molecules that exhibit decreased or a substantially nonexistent immunogenicity in an in vivo system.

These and other objects of the invention are provided for below.

In a compositional sense, the invention provides a peptide that selectively binds to colon cancer cells, the peptide preferably is a cyclic peptide. The peptide has the formula: A-X1-X2-X3-X4-X5-X6-X7-X8-X9-B, wherein X1-X9 each are an amino acid, wherein A and B are absent or are amino acids or peptides containing up to 6 amino acids, and wherein amino acids X2, X3, X4, and X5 may be the same or different and each optionally may be absent. Preferably, the peptide is cyclic and is made up of the sequence cys-pro-ile-glu-asp-arg-pro-met-cys (SEQ ID NO: 1), where the peptide contains a disulfide bond between the cys side chains.

In a methodological sense, the invention provides a method of diagnosing the presence of colon tumor cells in a patient. This method contains the steps of contacting a sample of colon cells obtained from the patient with a diagnostic composition of the invention, and detecting binding of the composition to colon tumor cells. The invention also provides methods of treating a patient suffering from colon cancer, comprising steps of administering to the patient a pharmaceutical composition of the invention.

BRIEF DESCRIPTION OF THE FIGURES

FIG. 3 shows evolution of the sequences obtained from successive rounds of maturation on HT29 cells.

FIG. 4 shows the dependence of HT29 binding on the presence of three amino acids, RPM, and their position within the peptide. CPIEDRPMC, CPIRPMEDC, CPIDERPMC, CALRDRPMC, CPEKFRPMC AND CSPQSQPMC sequences are disclosed as SEQ ID NOS 134, 137 and 142-145, respectively.

FIG. 5 shows binding data demonstrating that phage displaying peptides containing the RPM motif bind selectively and specifically to HT29 cells. CPIEDRPMC CKHLGPQLC, CPIEDRPMCGGS and CKHLGPQLCGGS sequences are disclosed as SEQ ID NOS 134-135 and 140-141, respectively.

FIG. 6 shows immunofluorescence data demonstrating that peptides containing the RPM motif bind selectively to HT29 cells.

FIG. 7 shows data demonstrating that binding of peptides containing the RPM motif to HT29 cells is stereospecific and that binding can be eliminated after protease treatment of the cells.

FIG. 9 shows immunofluorescence data demonstrating that a peptide containing the RPM motif binds to colon tumors. CPIEDRPMC sequence is disclosed as SEQ ID NO: 134.

FIG. 10 shows that a peptide containing the RPM motif does not bind to normal lung, liver or stomach or to liver or lung cancer.

FIG. 11 shows that a peptide containing the RPM motif conjugated to a cytotoxic agent can kill colon tumor cells. RPM-KLAK and KLAK sequences are disclosed as SEQ ID NOS 132-133, respectively.

DETAILED DESCRIPTION

Figure 1:
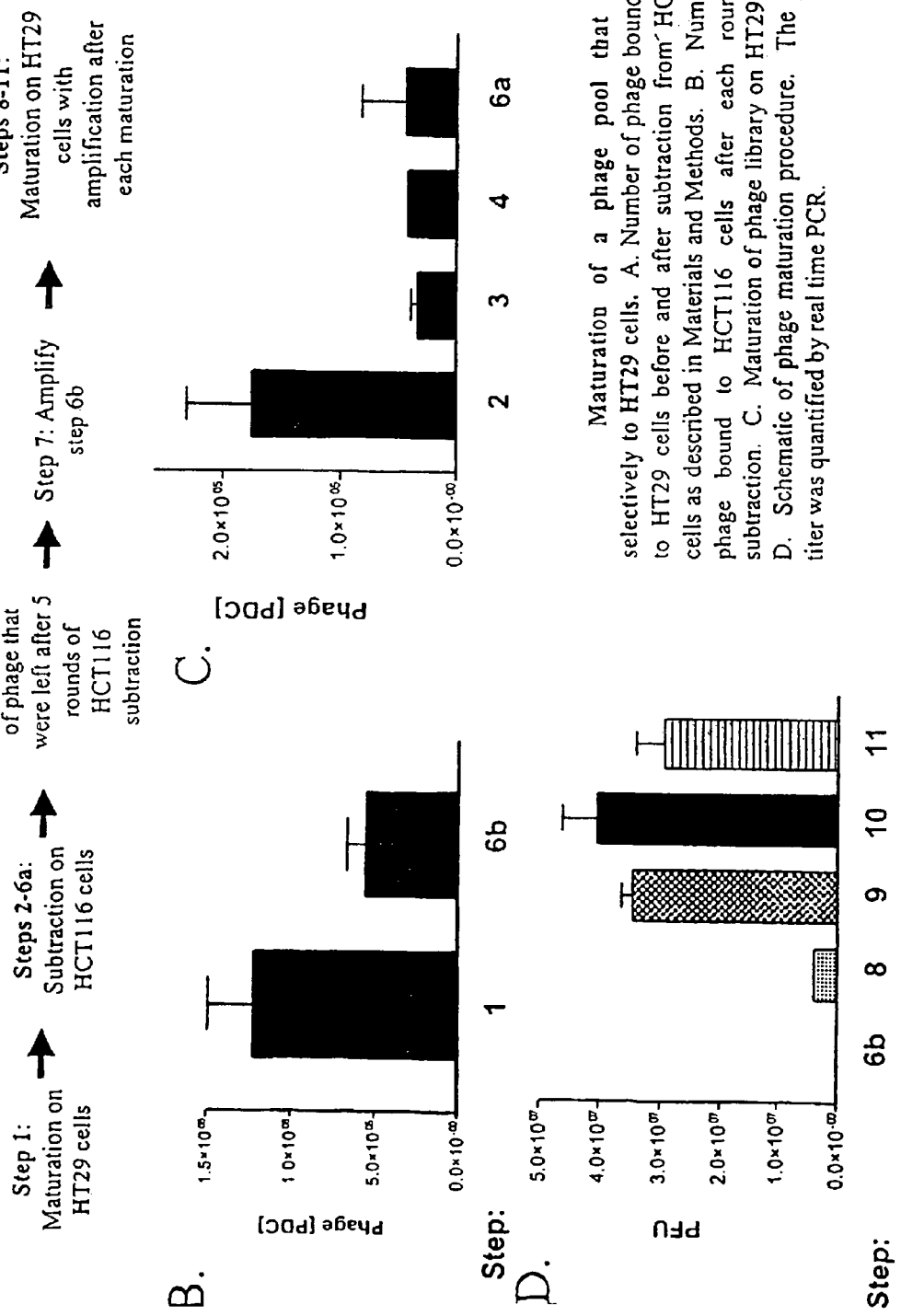
FIG. 1 shows the maturation of pool of peptides displayed on phage that binds selectively to HT29 cells.

The invention provides peptides that selectively bind to colon tumor cells, relative to normal colon cells, as well as methods for obtaining the same. Accordingly, peptides of the invention can be used in any number of contexts, e.g. to diagnose the presence of colon tumor cells in patient samples, and to treat colon cancer.

Identification of Certain Colon Tumor Specific Peptides:

The display of peptide libraries on the surface of bacteriophages was used to identify peptides with the desired binding properties.

The conventional use of phage display is to identify peptides that bind to homogenous target molecules in vitro. In an extension of phage display technology, Pasqualini & Ruoslahti, *Nature* 380:364-66 (1996), have reported the selection of peptides on a heterogeneous molecular population in the vasculature using in vivo phage display. Although the targeted endothelial cells of vasculature have a mixture of cell surface proteins with different affinities and conformations, injecting mice with peptide phage libraries led to the identification of specific peptides for these targets. Through this approach, peptides have been identified that "home" to vascular tissue.

Although peptides have been identified that bind to tissue specific vasculature, this in vivo phage display technique cannot be used to identify peptides that bind to cancer cells, as the phage are confined to the vasculature, i.e. where cancer cells are not. However, the present inventors surprisingly found that established cancer cell lines and "normal" cell lines could be use to obtain cancer cell specific peptides in vitro. Selection of cancer-specific peptides and their epitopes using peptide phage display libraries is a powerful method that allows direct identification of peptides that can be used for the diagnosis and treatment of colon cancer.

The role of phage display in the discovery of new drugs and diagnostics has been exemplified by the use of peptides identified by Pasqualini & Ruoslahti, supra, in conjunction with PET scan imaging of tumors and their use to selectively deliver toxins to cancer cells. When cell selective peptides are coupled to the apoptotic agent, TNFα, the efficacy:toxicity ratio of the coupled TNF was 14 times greater than with TNF alone.

In order to identify potential diagnostics and, therapeutics for neoplastic colonocytes, the present inventors used phage display to generate peptide libraries that distinguish between well-differentiated (HCT116) and poorly-differentiated colon carcinoma cells (HT29). The present inventors have developed a screening protocol that uses selection and subtraction on intact, viable cells, resulting in phage libraries that exhibit high binding selectivity for the poorly-differentiated HT29 cells. This approach allowed identification of peptides that are selective and specific for tumor cells, rather than cells of the vasculature.

Analysis of the selected library resulted in the identification of a nine amino acid, disulfide-constrained peptide having a three amino acid (arg-pro-met) motif (herein designated an "RPM" peptide) that specifically binds HT29 cells. Binding specificity was confirmed by showing that an RPM peptide successfully abolished binding of RPM-bearing phage to HT29 cells. In contrast, an unrelated peptide failed to block the RPM-phage binding. A majority of the sequences recovered after selection contained the RPM tripeptide motif directly adjacent to the C-terminal cysteine.

Further investigation proved that the binding of RPM to HT29 cells was not simply the result of non-specific charge interactions. In particular, a peptide synthesized with all D amino acids failed to compete for binding to the cells. Likewise, a peptide containing an RPM sequence in the middle of the peptide instead of adjacent to the C-terminus failed to compete for binding to HT29 cells. These data prove that binding to HT29 cells was dependent on the peptide sequence and not the phage proteins or non-specific interactions.

RPM was confirmed to be a functional consensus sequence by synthesizing alanine substitution mutants in the RPM sequence and determining their ability to compete for binding with wild type RPM. Mutating either the arginine or methionine to alanine resulted in an impaired ability of that sequence to compete for binding, while mutating the proline to an alanine resulted in a complete abrogation of the peptide's ability to compete. Further, moving the RPM motif to the middle of the peptide abolished the ability of that peptide to compete with the wild type RPM peptide, suggesting that the cysteine plays a role in RPM binding to HT29 cells.

In further confirmation studies, immunohistochemical staining using FITC-conjugated RPM peptide showed binding of RPM to tumor tissue from four patients. Adjacent normal tissue showed no binding of FITC-conjugated RPM. Once again, binding studies revealed that labeled RPM peptide competed with unlabeled RPM peptide, but not an unrelated peptide. In addition, RPM failed to stain a panel of non-colon tissues including lung, liver and stomach. The translation of the RPM peptide selectivity from colon cancer cell lines to human colon cancer was unexpected. Typically, immortalized cell lines seldom recapitulate the in vivo setting.

The inability of an all D amino acid RPM peptide to compete for phage binding to HT29 cells and the sensitivity of RPM binding to HT29 cells treated with proteases indicated that RPM recognizes a colon tumor specific cell surface protein.

Peptides of the Invention:

The peptides of the present invention offer a great benefit by circumventing the shortcomings of conventional diagnostic and treatment modalities, such as the use of antibodies, in that they are non-immunogenic or substantially non-immunogenic and combine high affinity and selectivity with more desirable pharmocokinetic properties than previously known drugs or proteins. The peptides contemplated by the invention provide an added benefit for tumor targeting by virtue of their ability to selectively deliver therapeutic agents, such as cytotoxic agents, to the tumor. Specific targeting using high affinity and high selectivity peptides permits use of low doses of anti-tumor agents, thereby eliminating or diminishing the toxic effects of conventional chemotherapeutics, such as doxorubicin.

The peptides of the invention generally can be represented by the formula:

A-X1-X2-X3-X4-X5-X6-X7-X8-X9-B, where X1-X9 each are an amino acid, and where A and B are absent or are amino acids or peptides containing up to 6 amino acids. Amino acids X2-X5 may be absent.

The peptides according to the invention are, therefore, relatively short, typically containing up to 15 amino acids.

X5 is asp, glu, ser, phe, gln, met, val;

X6 is arg, his, gln, phe, ser, pro;

X7 is pro, tyr, arg, or trp; and

X8 is met, ser, leu, or arg.

In another embodiment, the peptides contain a cyclic nonapeptide motif, where X1 and X9 are cys, X6-X8 are arg-pro-met, and X2 is pro, ala, val, asp, gln, phe, or ile; X3 is ile, leu, glu, met, pro, or his; X4 is glu, asp, his, arg, pro, ala, lys, gln, or ser; and X5 is asp, glu, ser, phe, gln, met, val.

In another embodiment, the peptides contain a cyclic nonapeptide motif, where X1 and X9 are cys, X6-X8 are arg-pro-met, X2 is pro; X3 is ile or leu; X4 is glu, asp, or arg; and X5 is asp or glu. In another embodiment, the peptides contain a cyclic nonapeptide motif, where X1-X9 is cys-pro-ile-glu-asp-arg-pro-met-cys (SEQ ID NO: 1). In each of the embodiments where X1 and X9 are cys, the peptide is cyclized via a disulfide bond between the side chains of X1 and X9. In yet another embodiment, the peptide contains a arg-pro-met-cys (SEQ ID NO: 2) motif, which may be constrained in a cyclic structure, wherein the cys-side chain forms a disulfide bond with another cysteine side chain located elsewhere in the peptide.

In yet further embodiments, X1 and X9 are cys, and X2-X8 are selected, respectively, from the group consisting of (SEQ ID NOS 6-112, respectively, in order or appearance):

| | | | | | |
|---|---|---|---|---|---|
| ALLPNKT | AQPLKQN | SMSSHRW | APSQRAQ | AYPYWLY | SNSQDQN |
| ELNAAHT | DHPVPWR | SPQSQPM | ETGYSFR | DLREHTL | SRLDSPF |
| ETLSPRD | DRIGARQ | SYDYAKH | FESQSRL | FESQSRL | THLMPLT |
| FMKTLSN | GTATLHW | TKSLLLA | HQLYRGL | HDSLYRA | TSPLPSQ |
| IQGSGST | HNPPRPQ | TSSTPKA | KASMKSP | HNVRFPN | TTRGPST |
| KATAMNS | HQSSPQL | VSLQPMT | LAHASNS | HQTNPNE | VSNQIAN |
| LAKVPAS | HSSHTHQ | VTTLNLT | MLPHGRT | IDPSLGL | NFNSRAS |
| IHPVPWR | NGTSRIQ | KAESPME | NLKQPEH | KATMTAT | NRALHSY |
| KDKDNLP | NSARWSV | KLVPTHQ | NSHDPEN | KNERAYL | NSKDPGT |
| KNLTHKH | NVTWGDT | KPTLPLS | PATPLKF | KQHHVTE | PKGSGMN |
| KQPTSNY | PNQGAYV | KSPSSLQ | PPAHHPN | KTPIPKI | QLPRSQS |
| KTTHPAL | QQSLSLI | LHMHQHI | QTPSLRL | LKQHWYS | SAHHPHA |
| LLPLAAP | SHQDPSL | LPHSQAH | SLSQPFR | LPSKFSH | SSRPPWN |
| LSASTLM | THSHKKP | LSPISLQ | TNPMRLH | LTPEPQY | TQLPVSW |
| NASLMSV | TTWWAST | NATQWQH | VHKFKPF | NGSYVWR | NPNSNDM |
| NSMPLHA | NWQPATH | PFGMVHT | PHPWPGK | PKMLGAA | PLTPTTV |
| PPHTLGL | PQELHPN | PSNETTQ | PSTAELA | PSYSTSY | PVSNLLQ |
| QPPMFYS | QPQSQPM | QTTPPFL | QWAALRP | and SLRTAAA. | |

The skilled artisan will recognize, however, that the peptides may contain as few as 5 amino acids and as many as 21. The skilled worker also will recognize that a peptide of the invention will contain any number of amino acids between 9 and 21, such as 10, 12, 14, 16, 18 and 20 amino acids.

In one embodiment, the peptides contain a central cyclic nonapeptide motif, where the peptide is cyclized via the side chains of X1 and X9. When A and B are absent, the peptide may be cyclized via formation of a lactam between the amino and carboxyl functions of X1 and X9. In a specific embodiment, X1 and X9 are both cysteine, and the peptide is cyclized via the formation of a disulfide bond between the two cysteine side chains.

In another embodiment, the peptides are represented by the above formula and contain a cyclic nonapeptide motif, where:

X1 and X9 are cys;

X2 is pro, ala, val, asp, gln, phe, or ile;

X3 is ile, leu, glu, met, pro, or his;

X4 is glu, asp, his, arg, pro, ala, lys, gln, or ser;

Mixtures or pools of the peptides in any combination may be used, but the invention also contemplates the use of a single type of peptide.

In the context of the present invention, a peptide is "selective" for binding to tumor cells when it binds at least about twice as strongly to tumor cells as to normal cells. A peptide is "specific" for binding to tumor cells when it binds about 5-10 times more strongly to tumor cells as to normal cells. Methods for measuring relative binding affinities are well known in the art.

As will be apparent by the following text, the invention contemplates the formulation of diagnostic and therapeutic compositions containing one or more peptides of the invention. Accordingly, the invention provides diagnostic compositions that contain a mixture of peptides, each of which can be conjugated to a detectable label, such as a radioactive or fluorescent marker. A peptide of the invention also can be conjugated to a detectable peptide moiety capable of specifically interacting with and/or being specifically bound by, another peptide or molecule. To this end, the detectable moiety may be a moiety such as a biotin molecule (which can bind to streptavidin), a peptide epitope that can be recognized and bound by a binding agent such as an antibody, (for example a FLAG peptide, to which a commercially available anti-flag antibody can bind), a Jun or Fos moiety (which are able to interact with each other) or any other epitope that is specifically recognized by a binding reagent, such as an antibody. Suitable conjugation moieties are well known in the art.

In addition, the invention contemplates pharmaceutical preparations, which contain a composition of peptides and a pharmaceutically acceptable sterile vehicle, carrier or excipient therefor. By "sterile" is meant a vehicle, carrier or excipient that does not bring about an intolerable immunogenic response when administered to a subject.

Therapeutic and Diagnostic Methods of the Invention:

Due to their properties, one or more peptides of the invention can, accordingly, be used in any number of methodologies. In particular, one or more peptides of the invention can be employed for diagnosis and/or treatment of disease. Thus, the invention provides methods of diagnosing the presence of colon tumor cells in a patient comprising the steps of administering to the paitent an effective amount of a diagnostic composition contemplated herein. The administered composition would, accordingly, bind to the colon tumor cells, and this binding can be detected by the presence of a detectable moiety, as described herein. By "effective amount" of a diagnostic composition is the amount needed to allow the skilled worker to determine if a patient is suffering from colon cancer.

The peptides of the invention also can find use in detecting the presence of tumors other than colon tumors. For example, the skilled worker will appreciate that certain peptides of the invention can be selective or specific for colon-derived tumors in other tissues or organs.

In the diagnostic setting, peptides of the present invention may be used to image or detect the presence of tumor cells in patients, either in vivo or ex vivo samples. Thus, for example, the peptide may be conjugated to (e.g., produced as a fusion protein with) a detectable label, such as a fluorescent dye or a radioactive label, to allow detection of peptide binding to a tumor cell taken as a biopsy. Methods of labeling peptides for this purpose are well known in the art. A peptide of the invention also can be produced as a fusion with an alternative detection moiety, as further described herein, e.g. biotin, FLAG, jun, fos or an epitope recognized by an antibody. Methods for detecting labeled peptides in vitro and in vivo also are well known in the art.

A peptide of the invention also may be conjugated with a therapeutic moiety for use in treating colon cancer. Suitable therapeutic moieties include, for example, cytotoxic drugs, such as drugs that interfere with intracellular protein synthesis, toxins, including toxins that lack an intact cell-binding domain, and radioactive moieties. Other therapeutic agents that can be linked to the peptide are known in the art. Drugs that interfere with intracellular protein synthesis are known to these skilled in the art and include puromycin, cycloheximide, and ribonuclease.

Toxins useful as therapeutics are known to those skilled in the art and include plant and bacterial toxins, such as, abrin, alpha toxin, diphtheria toxin, exotoxin, gelonin, pokeweed antiviral protein, ricin, and saporin. Toxins in their native form require a minimum of three different biochemical functions to kill cells: a cell binding function, a cytotoxic function, and a function to translocate the toxic activity into the cells. The modified toxins used in the present invention differ from native toxins in that the domain providing the cell binding function of the native toxin is nonfunctioning because the domain is missing partially or totally.

The drug or modified toxin is then treated by methods known to those skilled in the art to permit them to be conjugated to the protein containing at least one mercapto group. Methods for treating toxins and, in particular, modified Pseudomonas exotoxins, are disclosed in Batkra et al., Proc. Natl. Acad. Sci. USA, Vol. 86, pp. 8545-8549, 1989; Seetharam et al., The Journal of Biol. Chem., Vol. 266, No. 26, pp. 17376-17381, 1991; and Pastan et al., U.S. Pat. No. 4,892,827, all incorporated herein by reference. A preferred modified Pseudomonas exotoxin comprises ADP ribosylating activate, an ability to translocate across a cell membrane and devoid of a functional receptor binder region Ia of the native toxin. One such modified Pseudomonas exotoxin is devoid of amino acids 1-252 and 365-380 of native Pseudomonas exotoxin and contains a-KDEL (SEQ ID NO: 3) mutation instead of -REDLK (SEQ ID NO: 4) at the carboxyl terminus.

Peptides of the invention also are amenable to non-invasive methods for diagnosing tumors. Due to the ongoing sloughing off of cells in the colon, fecal material is likely to contain colon cells. A sample of fecal material, accordingly, could be prepared for screening with a peptide of the invention, on the basis that said peptide would specifically or selectively bind to an tumor cell contained in the feces.

With regard to therapeutic approaches, it previously has been shown that conjugating drugs to peptides specific for angiogenesis markers could eliminate tumors by destroying their vasculature (see U.S. Pat. No. 6,491,894). Despite such advance, however, anti-cancer therapy focused in the vasculator is ineffective against many tumors under 1 $mm^3$, which are able to exist in isolation from the vasculature by receiving their nutrients from adjacent normal blood vessels. Accordingly, therapy limited to the vasculature leaves the task of eliminating at least some portion of the tumor remaining.

Thus, another use of peptides of the invention (e.g., those isolated according to phage display selection methods described herein) is the coupling of peptides to cell toxins for therapeutic or treatment purposes, namely, to treat patients suffering from colon cancer. In this regard, the invention provides a process which entails administering the peptides in a form conjugated to a therapeutic agent, such as a cytotoxic moiety. The peptide binds to tumor cells in the patient and delivers the therapeutic agent selectively or specifically to those cells. Suitable therapeutic agents and methods of conjugating such agents to peptides are well known in the art.

Indeed, the present inventors have generated a reagent that can eliminate a tumor (including the remains of tumor not in contact with the vasculature) by binding selectively to cancer cells and, by being internalized, by carrying a toxin to the cells. In vitro, HT29 colon cancer cells were selectively killed by incubating them with RPM conjugated to a toxin. In contrast, HCT116 (non tumor) cells were not affected by treatment with RPM-(KLAK)$_2$ (SEQ ID NO: 5). This demonstrates an exquisite selectivity of RPM for HT29 cells, as well as the utility and promise of this approach for selectively destroying tumor cells while leaving normal cells intact or substantially unharmed. The peptide was shown to be internalized upon binding to the tumor cells.

Methods of Identifying Further Colon-Specific Peptides:

Other features contemplated by the invention include methods of identifying a homing molecule that homes to a marker on a colon tumor cell. The method includes the steps of contacting in vitro a substantially purified population of tumor cell lines (e.g., HT29 colon cancer cells) with one or more molecules and determining the specific binding of a molecule to the tumor cell vis-à-vis a non-neoplastic colon cell (e.g., HCT116), where the presence of specific binding identifies the molecule as a homing molecule that homes to a colon tumor cell.

Further homing molecules that home to a colon tumor can be identified by screening one or more molecules, for example, a library of molecules. As used herein, the term "library" means a collection of molecules. A library can contain a few or a large number of different molecules, varying from about ten molecules to several billion molecules or more.

Methods for preparing libraries containing diverse populations of various types of molecules such as peptides, peptoids and peptidomimetics are well known in the art and various libraries are commercially available (see, for example, Ecker and Crooke, Biotechnology 13:351-360 (1995), and Blondelle et al., Trends Anal. Chem. 14:83-92 (1995), and the references cited therein, each of which is incorporated herein by reference; see, also, Goodman and Ro, Peptidomimetics for Drug Design, in "Burger's Medicinal Chemistry and Drug Discovery" Vol. 1 (ed. M. E. Wolff; John Wiley & Sons 1995), pages 803-861, and Gordon et al., J. Med. Chem. 37:1385-1401 (1994), each of which is incorporated herein by reference). Where a molecule is a peptide, protein or fragment thereof, the molecule can be produced in vitro directly or can be expressed from a nucleic acid, which can be produced in vitro. Methods of synthetic peptide and nucleic acid chemistry are well known in the art.

A library of molecules also can be produced, for example, by constructing a cDNA expression library from mRNA collected from a cell, tissue, organ or organism of interest. Methods for producing such libraries are well known in the art (see, for example, Sambrook et al., Molecular Cloning: A laboratory manual (Cold Spring Harbor Laboratory Press 1989), which is incorporated herein by reference). Preferably, a peptide encoded by the cDNA is expressed on the surface of a cell or a virus containing the cDNA. For example, cDNA can be cloned into a phage vector such as fuse 5 (Example I), wherein, upon expression, the encoded peptide is expressed as a fusion protein on the surface of the phage.

The following working examples are illustrative embodiments of the invention are and do not, therefore, limit the invention.

EXAMPLES

Materials and Methods

Generation of HS-1. An aliquot (10 ul) of the C7C complete phage library from New England Biolabs (Beverley, Mass.) was incubated with $2 \times 10^5$ cells HT29 cells at 4C for 45 minutes in PBS with 0.5% BSA (binding buffer). After incubation, cells were washed with PBS/0.5% BSA/0.05% Tween (wash buffer) for a total of 6 washes. Phage that bound were eluted with 0.2M glycine (pH 2.2) for 8 minutes then neutralized with 50 uL of 1 M Tris-HCl (pH 9.0). After elution, phage were PEG-NaCl precipitated then resuspended in 300 uL of binding buffer and incubated with $2.0 \times 10^5$ HCT116 cells at 4° C. for 45 minutes a total of 5 incubations (steps 2-6). The phage that did not bind to the HCT116 cells were amplified (step 7) then incubated with $2 \times 10^5$ HT29 cells as above. Cells were washed to remove unbound phage and the bound phage was eluted. The number of phage bound was determined and the remaining eluate was amplified. The amplified phage was used with the same number of HT29 cells and the process was repeated (steps 9-12) for a total of five rounds of maturation. After the five rounds of selection, phage from each round was titered, plaques were picked, phage DNA amplified by PCR and finally, sequenced.

Synthesis of Peptides

Phage binding assay. HT29 cells were incubated with peptide in binding buffer at concentrations of 0, 0.1, 1, 10, 100, or 1000 µM for 30 minutes at 4° C. After 30 minutes of incubation, $10^{10}$ pfu of phage were added to the cells and incubated at 4° C. for an additional 45 minutes. Following incubation, cells were washed 6× with wash buffer and the phage remaining bound were eluted with glycine. The number of phage bound to the cells was quantified with real time PCR.

Immunohistochemistry

Cell Culture: HT29, HCT116, or a 50% mixture of HT29 and HCT116 cells were plated on glass slides (Nalge). Wells were incubated with 10 µM of RPM-FITC peptide for 45 minutes at 4° C. or 37° C. After washing with wash buffer, cells were blocked with 1% NGS, 0.1% BSA, 0.1% Triton-X100 in PBS. Following the blocking step, wells were incubated with the polyclonal p53 antibody, D10, (Santa Cruz) for 1 hour at room temperature. The wells were washed and incubated with the secondary antibodies GαFITC Alexa 488 (Molecular Probes) and GαMouse Alexa 647 (Molecular Probes) and the nuclear stain Topro-3 (Molecular Probes). Wells were washed and mounted using Pro-Long Anti-fade (Molecular Probes). Slides were analyzed by confocal microscopy.

Primary Tissue Analysis

A biopsy of sporadic colon adenocarcinoma, liver and lung sarcoma, and grossly uninvolved colon, liver, lung, and stomach were frozen in optimum cutting temperature (OCT) and 5-µM-thick cryostat sections placed on glass slides. Sections were stained with H&E and untreated adjacent sections were incubated with RPM-FITC. After incubating with RPM-FITC in binding buffer for 45 minutes at 4° C., slides were washed and mounted using Pro-Long Anti-Fade (Molecular Probes). Nuclei were visualized by a quick incubation with Topro-3 (Molecular Probes) present in the last wash. Samples were analyzed by confocal microscopy.

Protease Assay

HT29 cells were incubated at 37° C. with either active or boiled Collagenase diluted 1:20 for 10 minutes, Trypsin-EDTA 0.25% (Gibco) for 5 minutes or Proteinase K (Gibco) diluted 1:600 for 1 minute. After incubation, cells were then incubated with RPM bearing phage as described above. The number of phage remaining bound was quantified by real time PCR.

RPM-KLAK (SEQ ID NO: 132) and KLAK (SEQ ID NO: 133) on HT29 and HCT116 cells. HT29 and HCT116 cells were incubated with increasing log concentrations of RPM-KLAK (SEQ ID NO: 132) or KLAK (SEQ ID NO: 133) for 72 hours at 37° C. After incubation, MTT was added to a final concentration of 2.5 ug/mL and incubated at 37° C. for 1 hour. The media/MTT was removed carefully and the cells dissolved with 0.1N HCl in isopropanol. Absorbance was read on a plate reader (Cytofluor II, Perceptive Biosystems) at 570 nm.

Results

HS-1 library is selective for HT29 cells and contains a consensus binding motif. To identify potential molecular markers of colorectal cancer, phage display was used to generate peptide libraries that distinguish between well-differentiated (HCT116) and poorly-differentiated (HT29) colon carcinoma cells. In addition to having characteristics of poorly-differentiated tumor colonocytes, another distinguishing feature of HT29 cells is that the adenomatous polyposis coli (APC) gene, which is mutated in approximately 85% of colon cancers, is also mutated in HT29 cells. In contrast, HCT116 colon cancer cells contain wild-type APC. To identify cell surface proteins present only on HT29 cells, the present inventors used an M13 random, disulfide constrained, peptide phage display library, C7C, to select on cells at conditions (4° C.) that should inhibit internalization of the phage. Secreted and cell surface proteins are important among protein targets because they are useful as both diagnostic markers and targets for drug delivery. The mature HT29 cell selective library was named HS-1.

After generation of the HS-1 library, the effectiveness of the maturation scheme for generating a HT29 selective library was determined by testing the library for its ability to bind HT29 and HCT116 cells. A constant number of phage from the amplified pool of each round was incubated with HT29 or HCT116 cells and the number of phage present in the acid elution was quantified (FIG. 1a). After the initial round of maturation and subtraction, the number of phage binding to HT29 and HCT116 cells was equivalent. Following amplification and the second round of selection, a two-fold selectivity of the library for HT29 cells was evident. Maximum selectivity (ten-fold) of the library for HT29 cells occurred after the third round of selection and did not increase with further selection steps.

To demonstrate that the original phage library was unbiased toward the sequence RPM, phage from the first round of maturation were sequenced. RPM was absent from the sequences of the phage isolated from round 1. Two rounds of maturation showed the emergence of the RPM peptide with 4 out of 25 phage containing the RPM sequence. Nevertheless, round 2, similar to round 1, lacked a clear consensus sequence. Next, individual phage plaques from selection rounds 3 and 4, which were the rounds of maximal selectivity for HT29 cells, were isolated, and the DNA from each phage plaque was amplified by PCR then sequenced. Peptide sequences were compiled and analyzed for homology using Megalign alignment software. Despite the theoretical complexity of $10^9$ sequences in the starting population, a clear majority, 20/27, (FIG. 1B, rounds 3 and 4) expressed an identical peptide motif, RPM. Moreover, in round 3, 24 out of 27 phage and in round 4, 25 out of 27 phage contained at least the amino acids PM (FIG. 1B). Of the sequences examined, the RPM sequence was always found directly adjacent to the C-terminal cysteine.

RPM Peptide Binding to HT29 Cells is Selective and Mediated Through the Peptide Sequence.

Figure 2:
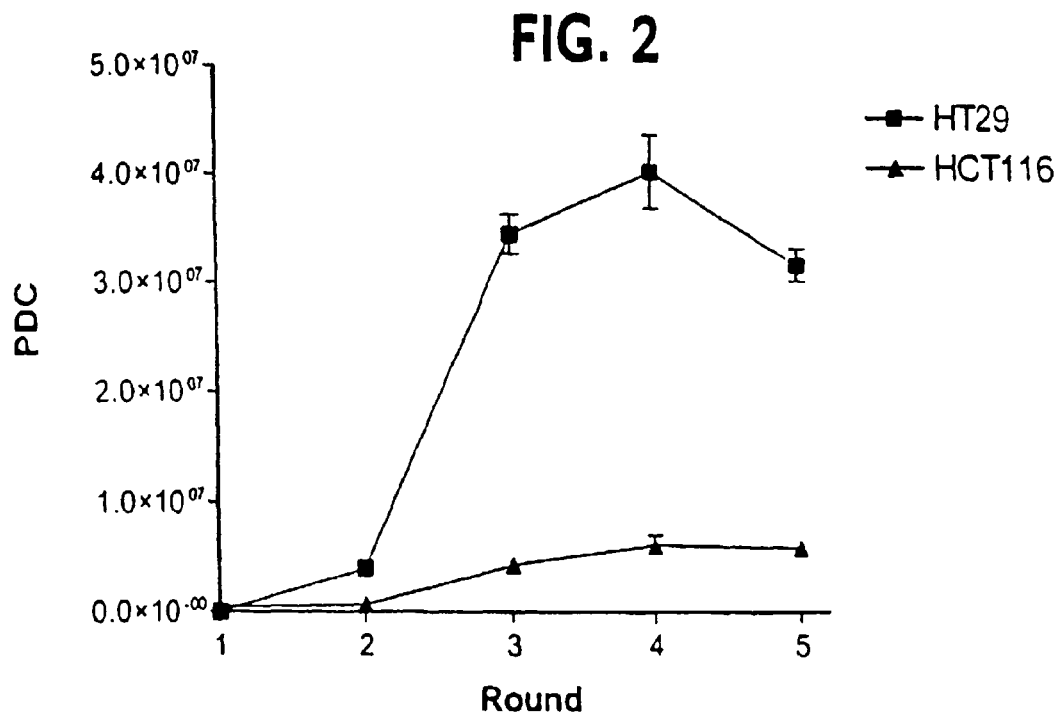
FIG. 2 shows selective binding of the phage pool to HT29 cells.
Figure 8:
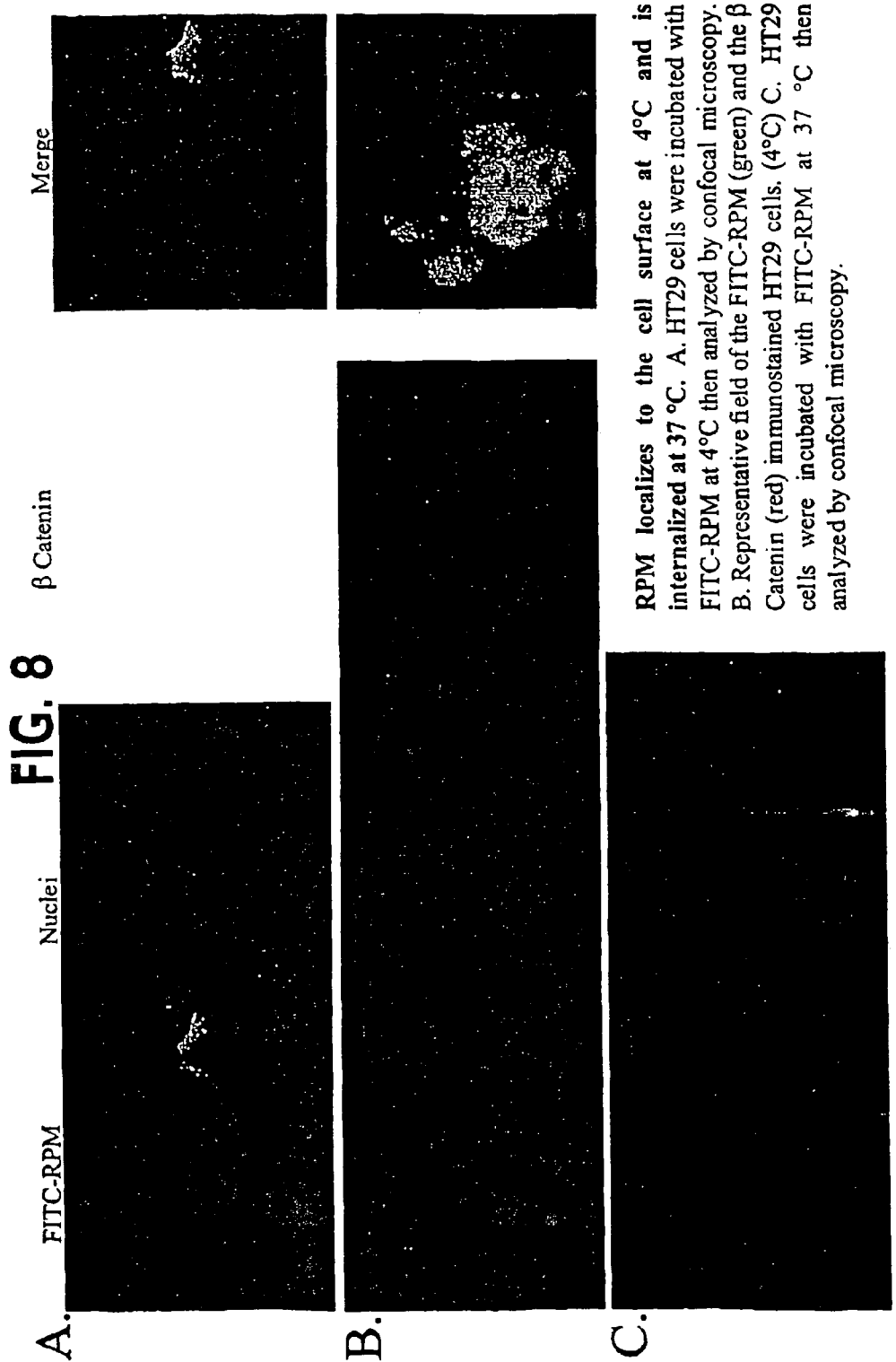
FIG. 8 shows that a peptide containing the RPM motif localizes to the cell surface at 4° C. and is internalized at 37° C.

The enrichment of peptides with the RPM sequence suggested that binding to HT29 cells depended on the peptide displayed by the phage and not on an incidental property of the phage. To determine whether CPIEDRPMC (SEQ ID NO: 134) displaying phage bind to HT29 cells specifically, a competition assay was performed using phage and synthetic peptides, peptides corresponding to the specific sequence, CPIEDRPMC (SEQ ID NO: 134), and the non-specific sequence, CKHLGPQLC (SEQ ID NO: 135), were synthesized by standard methods and oxidized to form a disulfide bond. Reaction of the peptides before and after oxidation with Ellman's reagent was performed to verify presence of the disulfide bond. CKHLGPQLC (SEQ ID NO: 135) was isolated from a previous screen for peptides that bound to HT29 cells and as such bound to HT29 cells. In FIG. 2A, HT29 cells were incubated with increasing log concentrations of CPIEDRPMC (SEQ ID NO: 134) peptide and with a constant number of either specific or non-specific phage. The number of phage binding to the HT29 cells was quantified and the percentage binding calculated based on the number of phage that bind in the absence of competitor. The sequence CPIEDRPMC (SEQ ID NO: 134) was competed with specific competitor but not with the non-specific competitor. Specific competitor reduced the level of RPM associated binding to HT29 cells to less than 4% whereas the level of binding to HT29 cells remained constant at 100% in the presence of non-specific competitor (FIG. 2A). The reciprocal experiment was also done with HT29 cells incubated with increasing log concentrations of specific or non-specific peptide and a constant concentration of phage displaying the peptide CPIEDRPMC (SEQ ID NO: 134). The results are similar to what was observed in FIG. 2A in that a peptide sequence corresponding to CPIEDRPMC (SEQ ID NO: 134) was able to compete phage bearing the same sequence but a peptide sequence CKHLGPQLC (SEQ ID NO: 135) was not able to compete phage bearing the CPIEDRPMC (SEQ ID NO: 134) sequence.

The peptide then was tested to determine whether it was able to differentiate HT29 from HCT116 cells. In order to distinguish HT29 from HCT116 cells in our immunohistochemical assays, staining was carried out in the presence of the transcription factor, p53. Staining for the protein p53 is a way to visually discriminate HT29 from HCT116 cells, since p53 is mutated and accumulates in HT29 cells but is wild type in HCT116 cells and thus, is rapidly degraded. As expected, immunohistochemical analysis of HT29 and HCT116 cells for p53 demonstrated a differential staining of HT29 and HCT116 cells with high levels of p53 expression detected in HT29 cells (FIG. 2B). To test the ability of the fluorescein conjugated peptide (RPM-FITC) to preferentially bind HT29 cells, HT29 and HCT116 cells were stained with RPM-FITC. After incubation for 1 hour at 4° C. with RPM-FITC, the HT29 cells showed fluorescence whereas the HCT116 cells exhibited little or no fluorescence (FIG. 2B). When a mixture of HT29 and HCT116 cells was incubated with RPM-FITC and concurrently analyzed for the presence of p53, cells with the highest level of p53 protein also bound RPM-FITC (FIG. 5A).

To determine whether RPM-FITC binding to HT29 cells was dependent on the peptide sequence, a competition assay was performed. HT29 cells were incubated with RPM-FITC and unlabeled specific or non-specific competitor. Specific competitor was able to abolish RPM-FITC staining of HT29 cells while RPM-FITC binding was unaffected by the presence of non-specific competitor.

RPM Binds to Human Colon Tumors But not to Normal Colon Lung, Liver, or Stomach, or to Liver or Lung Cancer.

Since the above data suggested that RPM was selective and specific for HT29 cells, it was determined whether RPM was able to bind and differentially stain human colon tumor as opposed to normal colon. A peptide-binding assay performed on frozen sections prepared from a biopsy sample of human colon tumor and grossly uninvolved normal colon showed the preferential binding of RPM-FITC to human colon tumor (FIG. 3). Tumors from four different patients were stained and all showed a staining pattern similar to that in FIG. 3 (data not shown). The ability of unlabeled specific competitor to abrogate binding to colon tumor shows that binding of RPM-FITC to colon tumor was mediated by RPM.

To determine whether RPM-FITC was able to bind cancers originated from tissues other than colon or to other normal tissues, a peptide-binding assay was performed on cryostat sections of lung and liver cancer, and grossly uninvolved lung, liver, and stomach. As a positive control, a section of colon tumor was stained in parallel with the other sections. FIG. 4 shows that lung and liver cancer as well as grossly uninvolved lung, liver, and stomach showed no labeling with RPM-FITC. In contrast, colon tumor exhibited bright staining when incubated with RPM-FITC.

Binding to HT29 Cells is Dependent on the Amino Acids, RPMC-C (SEQ ID NO: 136).

The ability of the peptide to bind selectively to human colon tumors was intriguing and prompted characterization of the interaction of the peptide with HT29 cells. The phage selection procedure produced naturally occurring substitution mutants so the phage and the peptide could be used to determine a functional consensus sequence for the family. HT29 cells were incubated with increasing log concentrations of CPIEDRPMC (SEQ ID NO: 134) peptide and a constant number of phage displaying one of the sequences were selected. The kinetics of competition were almost identical (within 2 fold) for the phage displaying the RPM motif. In contrast, the phage bearing the peptide sequence PM was competed at a 40 fold lower concentration of peptide than the phage bearing the RPM motif. The identity of the 4 residues before the RPM motif were unimportant and did not effect the ability of the peptide to compete with the phage for binding to HT29 cells.

The above assay narrowed the functional consensus sequence to RPM. To examine the importance of each residue within the RPM sequence for binding to HT29 cells, peptides were synthesized having alanine mutations in either the arginine, proline, or methionine residue and used in phage competition assay as described above. Mutations in the arginine or methionine had the same effect on the ability of peptide to compete an RPM displaying phage (FIG. 5B). The EC50 of competition shifted by ~100 fold from 5 uM with an RPM peptide to 690 and 545 uM using either the APM or RPA peptide. The peptide with the proline to alanine mutation was not able to compete with phage binding to HT29 cells at even 1 mM of peptide.

Since all of the peptides isolated from the selection contained the RPM motif at the C-terminal end of the peptide directly adjacent to the final cysteine, the importance of the cysteines for RPM binding activity was examined. A peptide was prepared bearing the RPM motif in the middle of the peptide (RPM middle), CPIRPMEDC (SEQ ID NO: 137), and used in the phage competition assays. FIG. 5C shows that the (RPM) middle peptide was over 100 fold less potent when compared to RPM in competing with the phage for HT29 cell binding.

RPM Peptide Binding to HT29 Cells is Consistent with Binding to a HT29 Protein.

Since protein-protein interactions typically depend on the chiral nature of the amino acids, an all D amino-acid RPM peptide was used in phage competition assay to try to determine if RPM was binding to a HT29 protein. HT29 cells were incubated with increasing log concentrations of either A11 D RPM or RPM and a constant number of RPM phage. After incubation, washing, and acid elution, the number of phage remaining bound was quantified. FIG. 6A shows that the binding of RPM to HT29 cells was dependent on the chiral nature of the amino acids since a RPM peptide consisting of all D amino acids was not able to compete with RPM phage for binding to HT29 cells.

The above data suggested that RPM was binding to a HT29 protein. In order to further this observation, HT29 cells were treated with active or boiled proteases to determine the effect of treatment on the ability of an RPM displaying phage to bind. HT29 cells were treated with active or boiled collagenase for 15 minutes, trypsin for 5 minutes, or proteinase K for 0.5 minutes at 37° C. After protease treatment, cells were washed, then an equal number of phage were added and allowed to bind. Quantification of the number of phage bound to the cells after protease treatment revealed that the ability of phage to bind to any of the active protease treated cells was decreased by 85, 90, and 90% (FIG. 6B). The decrease in phage binding to the HT29 cells was due to the protease activity since boiling the proteases abolished the effect with phage binding returning to levels of that observed for PBS treated cells (FIG. 6B). Treating the cells with proteases did not affect cell viability. After treating HT29 cells with proteases as described above, MTT was added to the cells and incubated for 45 minutes at 37° C. After incubation, the cells were solubilized with 0.1N HCl in isopropanol and the absorbance due to MTT incorporation was determined. The treated cells had an average absorbance of 0.188 (PBS), 0.189 (collagenase), 0.175 (trypsin), and 0.183 (proteinase K).

RPM is Internalized and Able to Selectively Deliver a Toxin to HT29 Cells.

The ability of a molecule to translocate across the cell membrane is important for drug delivery. HT29 cells were incubated for 1 hour at either 4° C. or 37° C. in the presence of 100 uM RPM-FITC. After incubation, cells were washed, fixed with 2% paraformaldehyde, then incubated with an anti-FITC secondary antibody to amplify the fluorescence signal. When the cells were incubated with RPM-FITC at 4° C., peptide binding was confined to the cell surface of the HT29 cells. In contrast, incubating HT29 cells with RPM-FITC at 37° C. revealed the presence of diffuse staining throughout the cells.

Since RPM-FITC is internalized at 37° C., RPM may be used to deliver a toxin to HT29 cells. To demonstrate this, an antimicrobial toxin, $(KLAK)_2$ (SEQ ID NO: 138), was used that selectively disrupts the mitochondrial membrane of eukaryotic cells while the cytoplasmic membrane remains intact. Cells that were incubated with $(KLAK)_2$ (SEQ ID NO: 138) alone or with free peptide were refractory to death induced by the toxin. However, when a peptide that was specific and also internalized by cells was conjugated to $(KLAK)_2$ (SEQ ID NO: 138), the cells were killed. RPM was coupled to $(KLAK)_2$ (SEQ ID NO: 138) and incubated with HT29 and HCT116 cells with either $(KLAK)_2$ (SEQ ID NO: 138) alone as a negative control or RPM-$(KLAK)_2$ (SEQ ID NO: 5). Cells were treated for 72 hours at 37° C. At the end of the incubation, cell viability was measured by MTT assay. As expected, incubation of either cell line with $(KLAK)_2$ (SEQ ID NO: 138) did not effect the viability of the cells (FIG. 7B). Since RPM should not bind to HCT116 cells, HCT116 cells should be resistant to death induced by RPM-$(KLAK)_2$ (SEQ ID NO: 5). This was indeed observed for HCT116 incubation with RPM $(KLALK)_2$ (SEQ ID NO: 5) (FIG. 6B). In contrast, HT29 cell viability was affected by incubation with RPM-$(KLAK)_2$ (SEQ ID NO: 5) in a concentration dependent manner with an LC50 of 0.31 uM.

What is claimed is:

1. A purified cyclic peptide that selectively binds to colon cancer cells wherein said peptide has the formula A-X1-X2-X3-X4-X5-X6-X7-X8-X9-B, wherein the sequence X6-X7-X8 is arg-pro-met.

2. The peptide according to claim 1 wherein said peptide comprises at least two cysteine amino acid residues, and wherein said peptide is cyclized via a disulfide bond between said two cysteine amino acid residues.

3. The peptide according to claim 1, wherein X1-X9 each are an amino acid, wherein A and B are absent or peptides containing up to 6 amino acids, and wherein amino acids X2, X3, X4, and X5 may be the same or different and each optionally may be absent.

4. The peptide according to claim 3, wherein X1 and X9 are cys, and the peptide contains a disulfide bond between the side chains of X1 and X9.

5. The peptide according to claim 4 wherein:

X2 is selected from the group consisting of pro, ala, val, asp, gln, phe, glu, ser, and ile;

X3 is selected from the group consisting of ile, leu, glu, met, pro, and his;

X4 is selected from the group consisting of glu, asp, his, arg, pro, ala, lys, gln, met, trp, and ser;

X5 is selected from the group consisting of asp, arg, ala, leu, glu, ser, phe, gln, met, and val.

6. The peptide according to claim 5 wherein X2 is pro, X3 is selected from the group consisting of ile and leu; X4 is selected from the group consisting of glu, asp, and arg; and X5 is selected from the group consisting of asp and glu.

7. A composition comprising at least two peptides according to any one of claims 1-5 and 6.

8. A cyclic peptide comprising the sequence cys-pro-ile-glu-asp-arg-pro-met-cys (SEQ ID NO: 1), wherein said peptide comprises a disulfide bond between the cys side chains.

9. A pharmaceutical preparation comprising a peptide or composition according to claim 1 in a pharmaceutically acceptable sterile vehicle.

10. A diagnostic composition comprising a peptide or mixture of peptides according to claim 1, wherein said peptide or peptides are conjugated to a detectable label.

11. A composition according to claim 10, wherein said detectable label is a fluorescent moiety or a radioactive label.

12. A composition comprising one or more peptides according to claim 1, wherein each of said peptides is conjugated to a therapeutic agent.

13. The composition according to claim 12, wherein said therapeutic agent is a cytotoxic agent.

14. A purified cyclic polypeptide represented by the formula A-cys-X1-X2-X3-X4-arg-pro-met-cys-B (SEQ ID NO: 139), wherein X1-X4 each are an amino acid, and wherein A and B are absent or peptides containing up to 6 amino acids.

* * * * *

SEQUENCE LISTING

<160> NUMBER OF SEQ ID NOS: 145

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(9)
<223> OTHER INFORMATION: cyclic peptide

<400> SEQUENCE: 1

Cys Pro Ile Glu Asp Arg Pro Met Cys
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Pro Met Cys
1

<210> SEQ ID NO 3
<211> LENGTH: 4
<212> TYPE: PRT
<213> ORGANISM: Pseudomonas sp.

<400> SEQUENCE: 3

Lys Asp Glu Leu
1

<210> SEQ ID NO 4
<211> LENGTH: 5
<212> TYPE: PRT
<213> ORGANISM: Pseudomonas sp.

<400> SEQUENCE: 4

Arg Glu Asp Leu Lys
1               5

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Pro Met Lys Leu Ala Lys Lys Leu Ala Lys
1               5                   10

<210> SEQ ID NO 6
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Ala Leu Leu Pro Asn Lys Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Gln Pro Leu Lys Gln Asn
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Met Ser Ser His Arg Trp
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Pro Ser Gln Arg Ala Gln
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Tyr Pro Tyr Trp Leu Tyr
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Asn Ser Gln Asp Gln Asn
1               5
```

```
<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Leu Asn Ala Ala His Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp His Pro Val Pro Trp Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Pro Gln Ser Gln Pro Met
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Thr Gly Tyr Ser Phe Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Leu Arg Glu His Thr Leu
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 17

Ser Arg Leu Asp Ser Pro Phe
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Thr Leu Ser Pro Arg Asp
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Arg Ile Gly Ala Arg Gln
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Tyr Asp Tyr Ala Lys His
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Glu Ser Gln Ser Arg Leu
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Glu Ser Gln Ser Arg Leu
1               5
```

```
<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr His Leu Met Pro Leu Thr
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe Met Lys Thr Leu Ser Asn
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Thr Ala Thr Leu His Trp
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Lys Ser Leu Leu Leu Ala
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

His Gln Leu Tyr Arg Gly Leu
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 28

His Asp Ser Leu Tyr Arg Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Ser Pro Leu Pro Ser Gln
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Gln Gly Ser Gly Ser Thr
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

His Asn Pro Pro Arg Pro Gln
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Ser Ser Thr Pro Lys Ala
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Ala Ser Met Lys Ser Pro
1               5
```

```
<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

His Asn Val Arg Phe Pro Asn
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Thr Arg Gly Pro Ser Thr
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Ala Thr Ala Met Asn Ser
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

His Gln Ser Ser Pro Gln Leu
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Ser Leu Gln Pro Met Thr
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 39

Leu Ala His Ala Ser Asn Ser
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

His Gln Thr Asn Pro Asn Glu
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Val Ser Asn Gln Ile Ala Asn
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Ala Lys Val Pro Ala Ser
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

His Ser Ser His Thr His Gln
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Val Thr Thr Leu Asn Leu Thr
1               5
```

```
<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Met Leu Pro His Gly Arg Thr
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Asp Pro Ser Leu Gly Leu
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asn Phe Asn Ser Arg Ala Ser
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ile His Pro Val Pro Trp Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asn Gly Thr Ser Arg Ile Gln
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 50

Lys Ala Glu Ser Pro Met Glu
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asn Leu Lys Gln Pro Glu His
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Ala Thr Met Thr Ala Thr
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asn Arg Ala Leu His Ser Tyr
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Asp Lys Asp Asn Leu Pro
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asn Ser Ala Arg Trp Ser Val
1               5
```

```
<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Leu Val Pro Thr His Gln
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asn Ser His Asp Pro Glu Asn
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Asn Glu Arg Ala Tyr Leu
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asn Ser Lys Asp Pro Gly Thr
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Asn Leu Thr His Lys His
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 61

Asn Val Thr Trp Gly Asp Thr
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Pro Thr Leu Pro Leu Ser
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Pro Ala Thr Pro Leu Lys Phe
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Lys Gln His His Val Thr Glu
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Pro Lys Gly Ser Gly Met Asn
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Lys Gln Pro Thr Ser Asn Tyr
1               5
```

```
<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Pro Asn Gln Gly Ala Tyr Val
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Ser Pro Ser Ser Leu Gln
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Pro Pro Ala His His Pro Asn
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Thr Pro Ile Pro Lys Ile
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Leu Pro Arg Ser Gln Ser
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 72

Lys Thr Thr His Pro Ala Leu
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Gln Ser Leu Ser Leu Ile
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu His Met His Gln His Ile
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Thr Pro Ser Leu Arg Leu
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Lys Gln His Trp Tyr Ser
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Ala His His Pro His Ala
1               5
```

```
<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Leu Pro Leu Ala Ala Pro
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser His Gln Asp Pro Ser Leu
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Pro His Ser Gln Ala His
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Leu Ser Gln Pro Phe Arg
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Pro Ser Lys Phe Ser His
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 83

Ser Ser Arg Pro Pro Trp Asn
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Ser Ala Ser Thr Leu Met
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr His Ser His Lys Lys Pro
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Leu Ser Pro Ile Ser Leu Gln
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Asn Pro Met Arg Leu His
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Leu Thr Pro Glu Pro Gln Tyr
1               5
```

```
<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Thr Gln Leu Pro Val Ser Trp
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asn Ala Ser Leu Met Ser Val
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Thr Thr Trp Trp Ala Ser Thr
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asn Ala Thr Gln Trp Gln His
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Val His Lys Phe Lys Pro Phe
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 94

Asn Gly Ser Tyr Val Trp Arg
1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asn Pro Asn Ser Asn Asp Met
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asn Ser Met Pro Leu His Ala
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asn Trp Gln Pro Ala Thr His
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Pro Phe Gly Met Val His Thr
1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Pro His Pro Trp Pro Gly Lys
1               5
```

```
<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Pro Lys Met Leu Gly Ala Ala
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Pro Leu Thr Pro Thr Thr Val
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Pro Pro His Thr Leu Gly Leu
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Pro Gln Glu Leu His Pro Asn
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Pro Ser Asn Glu Thr Thr Gln
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 105

Pro Ser Thr Ala Glu Leu Ala
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Pro Ser Tyr Ser Thr Ser Tyr
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Pro Val Ser Asn Leu Leu Gln
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gln Pro Pro Met Phe Tyr Ser
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Pro Gln Ser Gln Pro Met
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Thr Thr Pro Pro Phe Leu
1               5
```

```
<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Trp Ala Ala Leu Arg Pro
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ser Leu Arg Thr Ala Ala Ala
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Val Pro Glu Gln Arg Pro Met
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Glu Leu Ser Arg Arg Pro Met
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Pro Glu Lys Phe Arg Pro Met
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 116

Pro Met His Gln Arg Pro Met
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Pro Ile Glu Asp Arg Pro Met
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Pro Ile His Asp Arg Pro Met
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Leu Arg Asp Arg Pro Met
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Pro Gln Leu Arg Pro Met
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Pro Glu Trp Ala Arg Pro Met
1               5

```
<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Pro Leu Asp Lys Arg Pro Met
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Leu Glu Arg Arg Pro Met
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Glu Leu Trp Gln Arg Pro Met
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Asp Leu Pro Met His Pro Met
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Pro Ile Asp Glu Arg Pro Met
1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 127

Pro Leu Ala Ser Arg Pro Met
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Pro Glu Lys Phe Arg Pro Met
1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Pro Met His Gln Arg Pro Met
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Val Pro Glu Gln Arg Pro Met
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asp Leu Pro Met His Pro Met
1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Arg Pro Met Lys Leu Ala Lys
1               5

```
<210> SEQ ID NO 133
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Lys Leu Ala Lys
1

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Cys Pro Ile Glu Asp Arg Pro Met Cys
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Cys Lys His Leu Gly Pro Gln Leu Cys
1               5

<210> SEQ ID NO 136
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Arg Pro Met Cys Cys
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Cys Pro Ile Arg Pro Met Glu Asp Cys
1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 138

Lys Leu Ala Lys Lys Leu Ala Lys
1               5

<210> SEQ ID NO 139
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: 0-6 variable amino acid residues
<220> FEATURE:
<221> NAME/KEY: MOD_RES
<222> LOCATION: (8)..(11)
<223> OTHER INFORMATION: Variable amino acid
<220> FEATURE:
<221> NAME/KEY: MOD_RES
<222> LOCATION: (16)..(21)
<223> OTHER INFORMATION: 0-6 variable amino acid residues

<400> SEQUENCE: 139

Xaa Xaa Xaa Xaa Xaa Xaa Cys Xaa Xaa Xaa Xaa Arg Pro Met Cys Xaa
  1               5                  10                  15

Xaa Xaa Xaa Xaa Xaa
            20

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Cys Pro Ile Glu Asp Arg Pro Met Cys Gly Gly Ser
1               5                  10

<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Cys Lys His Leu Gly Pro Gln Leu Cys Gly Gly Ser
1               5                  10

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Cys Pro Ile Asp Glu Arg Pro Met Cys
1               5
```

```
<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Cys Ala Leu Arg Asp Arg Pro Met Cys
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Cys Pro Glu Lys Phe Arg Pro Met Cys
1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Cys Ser Pro Gln Ser Gln Pro Met Cys
1               5
```